United States Patent [19]
Cheong

[11] Patent Number: 5,571,529
[45] Date of Patent: Nov. 5, 1996

[54] METHOD OF MAKING POLYURETHANE FOAM

[75] Inventor: Catherine L. Cheong, Burnley, England

[73] Assignee: Johnson & Johnson Medical, Inc., Arlington, Tex.

[21] Appl. No.: 971,440

[22] Filed: Nov. 4, 1992

[30] Foreign Application Priority Data

Nov. 7, 1991 [GB] United Kingdom ............... 9123708

[51] Int. Cl.⁶ .................. A61L 15/26; A61F 13/00; C08J 9/08; C08G 18/10
[52] U.S. Cl. .................. 424/445; 424/443; 424/447; 521/117; 521/130; 521/159; 602/46; 206/440; 53/425; 53/426
[58] Field of Search .................. 521/117, 130, 521/159; 424/443, 445, 447; 602/46; 206/440; 53/425, 426

[56] References Cited

U.S. PATENT DOCUMENTS

| | | | |
|---|---|---|---|
| 2,993,013 | 7/1961 | Wolfe, Jr. | 521/67 |
| 3,178,300 | 4/1965 | Gemeinhaerdt et al. | 106/122 |
| 4,127,124 | 11/1978 | Clagett et al. | 521/159 |
| 4,158,087 | 6/1979 | Wood | 521/137 |
| 4,339,550 | 7/1982 | Palinczar et al. | 521/99 |
| 4,454,251 | 6/1984 | Frisch et al. | 521/170 |
| 4,655,210 | 4/1987 | Edenbaum et al. | 128/156 |
| 4,715,746 | 12/1987 | Mann et al. | 521/117 |
| 4,725,627 | 2/1988 | Arnason et al. | 521/65 |
| 4,733,659 | 3/1988 | Edenbaum et al. | 128/156 |
| 4,920,172 | 4/1990 | Daoud | 524/502 |
| 4,950,695 | 8/1990 | Stone | 521/157 |
| 4,960,594 | 10/1990 | Honeycutt | 424/445 |
| 4,986,928 | 1/1991 | Merchant | 521/131 |
| 5,064,653 | 11/1991 | Sessions et al. | 424/445 |
| 5,065,752 | 11/1991 | Sessions et al. | 128/156 |
| 5,227,408 | 7/1993 | Hanna et al. | 521/908 |

FOREIGN PATENT DOCUMENTS

| | | |
|---|---|---|
| 0171268 | 2/1986 | European Pat. Off. |
| 0335669 | 10/1989 | European Pat. Off. |
| WO88/01878 | 3/1988 | WIPO |

*Primary Examiner*—James J. Seidleck
*Assistant Examiner*—Rabon Sergent
*Attorney, Agent, or Firm*—Andy C. Farmer; James Riesenfeld

[57] ABSTRACT

A polyurethane foam suitable for use as a wound-contact layer in a wound dressing is made by mixing 1 part by weight of an isocyanate-capped prepolymer having from 0.5 to 1.2 meq NCO groups/g with from 0.4 to 1.0 parts by weight of water in the presence of from 0.05 to 0.4 parts by weight of a $C_1$ to $C_3$ monohydric alcohol, and then drying the product. The monohydric alcohol is preferably methanol, and the isocyanate-capped prepolymer is preferably an isocyanate-capped ethyleneoxy/propyleneoxy copolymer.

23 Claims, 2 Drawing Sheets

METHOD OF MAKING POLYURETHANE FOAM

This invention relates to a method of making a polyurethane foam, and more particularly to a method of making a conformable, high-density polyurethane foam. The invention also relates to a wound dressing having a wound-contacting layer formed from such a foam.

Polyurethane foams have been proposed for a number of uses in the prior art. For example, U.S. application Ser. No. 3903232 discloses hydrophilic cross-linked polyurethane foams, which are said to be useful for the absorption of body fluids and may be used for external body cleaning, for internal body usage, and as absorptive products such as diapers. The foams are prepared by reacting particular isocyanate-capped polyoxyethylene polyols having an isocyanate functionality greater than 2 with large amounts of an aqueous reactant, preferably water.

EP-A-0171268 discloses a dressing for use in deep wounds, which dressing comprises individual pieces of an absorbent hydrophilic foam contained within a porous bag formed from an apertured polymeric film. The absorbent foam is preferably a hydrophilic polyurethane foam which can be made from HYPOL isocyanate-capped polyether prepolymer marketed by W. R. Grace & Co., and non-ionic surfactants.

According to EP-A-0171268, the fact that the foam is present in the form of individual pieces confers on the dressing the property of being able to conform to the contours of a wound cavity both on initial application of the dressing and subsequently following absorption of body fluids. It is said that existing commercially available foams, if used as a single piece, have too high a density to possess the required degree of conformability.

U.S. application Ser. No. 4339550 discloses a hydrophilic foam composition which is prepared by the "in situ" reaction of an isocyanate-capped polyether prepolymer having a functionality of from about 2 to about 8, water, and a chemically compatible, essentially non-polar, volatile organic compound. The foam is stated to be capable of achieving a sustained, controlled release of the volatile materials from the foamed structure. Suitable "control release" ingredients include polyols, such as propylene glycol and glycerine.

EP-A-0335669 discloses a hydrophilic foam composition comprising the "in situ" reaction product of an isocyanate-capped polyether prepolymer, a hydrophilic agent capable of absorbing water, an adjuvant comprising an alcohol, a wetting agent and water. One application which is proposed for the foam composition is in the manufacture of wound dressings. The composition is said to carry the adjuvant releasably, so that at least a portion of the adjuvant is released into an external liquid (e.g. wound exudate) with which the foam composition comes into contact.

A wide range of prepolymers, hydrophilic agents, adjuvants and wetting agents are proposed in EP-0335669. Suitable prepolymers are said to include prepolymers having an NCO content as high as 2.55 meq/g or as low as 0.5 to 0.9 meq/g. Water soluble monohydric, dihydric and polyhydric alcohols are all said to be suitable adjuvants, but glycerol is preferred, and the majority of the examples involve the use of glycerol. The sole example in which a monohydric alcohol is employed as the adjuvant involves the use of a prepolymer having an NCO content of 1.6 meq/g. The resulting product is said not to be acceptable because of "gross porosity".

The present invention is based on the unexpected finding that an isocyanate-capped prepolymer can be foamed in the presence of a $C_1$ to $C_3$ alcohol, without gross porosity in the resulting foam, if the NCO content of the prepolymer is less than 1.2 meq/g. indeed, far from having the undesirable characteristics suggested by EP-A-0335669, the resulting foams display the combination of high density and high conformability which EP-A-0171268 indicates to be unattainable in prior art foams.

Accordingly, the present invention provides a method of forming a polyurethane foam suitable for use as a wound-contacting layer, said method comprising mixing 1 part by weight of an isocyanate-capped prepolymer having from 0.5 to 1.2 meq NCO groups/g with from 0.4 to 1.0 parts by weight of water in the presence of from 0.05 to 0.4 parts by weight of a $C_1$ to $C_3$ monohydric alcohol, and then drying the product.

Isocyanate-capped prepolymers having a relatively low isocyanate content, such as those used in the method of the present invention, have been used in the prior art to produce so-called hydrogels. For this purpose, the prepolymers are mixed with relatively large quantities (eg. a ten-fold excess by weight) of water. The reaction mixture is initially of low viscosity, such that carbon dioxide which is evolved by reaction of the water with isocyanate end groups escapes. In this way, substantially no carbon dioxide is trapped within the hydrogel end product.

In contrast, the use of a relatively small amount of water in accordance with the present invention produces an initial reaction mixture of much higher initial viscosity. Carbon dioxide formed by hydrolysis of isocyanate end groups is therefore trapped, producing a foamed hydrogel.

Foams produced according to the method of the invention have a density of at least 0.28 $g/cm^3$, and preferably at least 0.30 $g/cm^3$. Particularly preferred foams have a density in the range 0.32 to 0.48 $g/cm^3$, e.g. about 0.35 $g/cm^3$.

The foams of the invention also have an elongation at break of at least 150%, and more preferably at least 300%. Particularly preferred foams according to the invention have an elongation at break in the range from 500 to 2000%.

Depending on the proportions of other additives, the foams of the invention have an absorbency of at least 3 g saline/g, preferably at least 5 g/g, and more preferably from 8 to 20 g/g. The foams are thus highly absorbent, yet conformable.

The foams of the invention also have the property of swelling and expanding when water is absorbed. This is particularly advantageous in a wound contact layer, because the swelling of the foam causes it to move inwards towards the wound bed, thus filling the wound cavity. This encourages the wound to heal from the base upwards and outwards, and it discourages epithelialization over the wound surface before the bed has been filled with granulation tissue.

The degree of swelling of the foams of the present invention on complete saturation with an aqueous medium is typically at least 100% (expressed in terms of increase in volume), and preferably at least 200%. Preferred foams swell by 400 to 800%. Despite this high degree of swelling, however, the foams of the invention retain their integrity even after absorption of large quantities of water.

Moreover, the foams are found to have a morphology which is particularly appropriate for low adherence wound dressings. The foams are open-celled, the cells being very regular in size and shape, with very smooth edges to the pores in the walls of the cells. Typically, the cells of the foams of the invention have an average diameter in the range 0.1 to 0.6 mm.

The prepolymer which is used in the method of the invention is preferably an isocyanate-capped polyether, such as an ethyleneoxy/propyleneoxy copolymer. A particularly suitable prepolymer is that available under Trade Mark HYPOL Hydrogel.

Although the invention comprehends the use of any of methanol, ethanol or propanol, the use of methanol is particularly preferred. All three alcohols reduce the rate of reaction between the isocyanate-capped prepolymer and water, but the effect of methanol is more marked. A reduction of the reaction rate is desirable in order to facilitate mixing of the various components and spreading of the reaction mixture into a layer of suitable thickness for curing.

It will be appreciated that other components may be added to the reaction mixture in the method of the invention, in order to give desired properties to the product. In particular, it is preferable to include a small proportion (e.g. up to 30% by weight of the wet composition) of a rubber, which may be either natural or synthetic. This has the effect of increasing the cure time for the polyurethane, and increases extensibility, strength and tack. Most importantly, it substantially reduces shrinkage of the gel on drying, and it also improves bubble formation, producing more regular, smaller bubbles.

Preferably, the rubber is added in the form of a latex, ie. a suspension or emulsion of the rubber in an aqueous medium. The latex will generally comprise 40 to 70% solids by weight, e.g. 50 to 60% by weight. If the foam is to be used as a wound contact layer, the rubber must of course be pharmaceutically acceptable.

Acrylic-based rubbers are particularly preferred. These are commercially available in the form of latexes, such as PRIMAL N-582 and RHOPLEX N-560, manufactured by the Rohm & Haas company.

In addition to the methanol or ethanol, other alcohols, and particularly polyols, may be included in the reaction mixture to produce a softer, more conformable foam. For example, a polyol sold by Bayer AG under the Trade Mark Levagel may be used. However, traces of such alcohols are likely to remain in the free form after the foaming reaction, and these traces may be difficult to remove from the foam merely by heating. The use of higher boiling alcohols is therefore preferably avoided if the foam is to be used as a wound contact layer, because of the likelihood that such alcohols will be leached from the foam during use of the dressing. When used as or in wound dressings, the foams of the invention preferably contain less than 1% by weight of water soluble alcohols, and more preferably less than 0.1% by weight. It is particularly preferred that the foams of the invention are essentially free of water soluble alcohols (eg. less than 0.01% by weight).

For use as a wound-contact layer, the foams of the invention may also include topical medicaments and antiseptics, such as silver sulphadiazine, povidone iodine, chlorhexidine acetate and chlorhexidine gluconate, as well as other therapeutically useful additives such as polypeptide growth factors and enzymes.

The present invention also provides a wound dressing comprising a wound contact layer formed from a polyurethane foam as described above, in conjunction with a water-repellant or water-impermeable backing layer. It is greatly preferred that the backing layer also be moisture vapour permeable, as well as being extensible and conformable. A particularly suitable material is a high density polyurethane foam, such as MEDIFIX 4003 or 4005. These are polyurethane foams of a blocked toluene diisocyanate nature, and are predominantly closed cell.

A particularly advantageous presentation for the dressing of the invention is as an island of wound-contact material on a backing layer, wherein at least the marginal portions of the backing layer are coated with adhesive. Any medically accepted, skin friendly adhesive is suitable, including acrylic, hydrocolloid, polyurethane and silicone based adhesives.

The adhesive may be applied either continuously or discontinuously over the marginal portions of the backing layer. Preferably, however, the adhesive is applied continuously over the whole of the backing layer if the backing layer is not itself impermeable to bacteria, so as to ensure that the backing layer/adhesive combination is impermeable to bacteria.

It is also preferred that the combination of adhesive and backing layer have a minimum moisture vapour permeability of 400 $g/m^2/24$ hrs, and preferably at least 700 $g/m^2/24$ hrs.

The preferred adhesive is a polyurethane gel material known as LEVAGEL and marketed by Bayer AG. This adhesive is made up of three components, namely a modified diphenylmethane diisocyanate, high molecular weight polyhydroxy polyether and a catalyst (dibutyltindilaurate). These three components may be mixed such that the gel contains 4–10 parts (preferably 4.6–6.4 parts) of the modified diphenylmethane diisocyanate, 99.9–99.9975 parts, (preferably 99.94–99.995 parts) of the polyhydroxy polyether and 0.0025–0.1 parts (preferably 0.005–0.06 parts) of the catalyst. The gel may be mixed by the methods given in U.S. Pat. No. 4,661,099 and applied by conventional coating methods to the backing. The thickness of the gel layer may be between 0.001 mm and 1.0 mm, and preferably between 0.05 mm and 0.5 mm, giving a coating weight of between 25 $g/m^2$ and 250 $g/m^2$.

The dressing may also contain a wicking layer between the wound contact layer and the backing layer. Such a wicking layer provides absorbency, but more importantly it encourages moisture to move from the wound facing side of the dressing to the back of the dressing where it escapes out of the dressing through the breathable backing. It should have good wicking properties so that moisture can be spread over as large a surface area as possible, thus increasing evaporation. The overall effect of this layer is to draw moisture from the wound facing layer, thus decreasing the chances of wound maceration, and to increase evaporation through the backing of the dressing.

The wicking layer may be formed of several plies (which may or may not be the same) if desired, but it is preferred that the total thickness of the wicking layer does not exceed 1 mm. It is also preferred that the wicking layer be substantially the same size and shape as the wound-facing layer, or slightly smaller than the wound-facing layer.

Suitable materials for the wicking layer include nonwoven, woven and knitted fabrics. Nonwoven viscose fabrics such as those conventionally used for making nonwoven surgical swabs are preferred, but it will be understood that many alternative fabrics (particularly other cellulosic fabrics) could be used in their place.

The dressings of the invention will generally be sterile and enclosed in a conventional bacteria-proof envelope. Sterilization may conveniently be carried out using γ irradiation, but other sterilization methods such as electron beam sterilization may also be used.

BRIEF DESCRIPTION OF THE DRAWINGS

The present invention is further illustrated by the following examples and with reference to the accompanying drawings, in which.

PREPARATION OF POLYURETHANE FOAM

EXAMPLE 1:

Methanol (6 g) was added to HYPOL Hydrogel prepolymer (50 g; NCO content 0.5–1.2 meq/g) in a disposable cup and mixed thoroughly for a few seconds. Water (44 g) was then added to the HYPOL mixture and stirred vigorously. The foaming mixture was poured onto release paper and spread using a stainless steel hand spreader set at a gap of 2.2 mm. The foam was left to cure and the foam sheet and release paper were placed in an oven (80°–100° C.) (30 min) to drive off the water. After cooling, the foam was lifted from the release paper, allowed to shrink, and replaced on the same paper. The foam was then kiss-cut to size and shape.

In an alternative procedure, the components were mechanically mixed using a commercially available two component polyurethane meter/mix dispense machine. The HYPOL prepolymer was placed in one pot and the water and methanol were pre-mixed and placed in the second pot.

Figure 1:
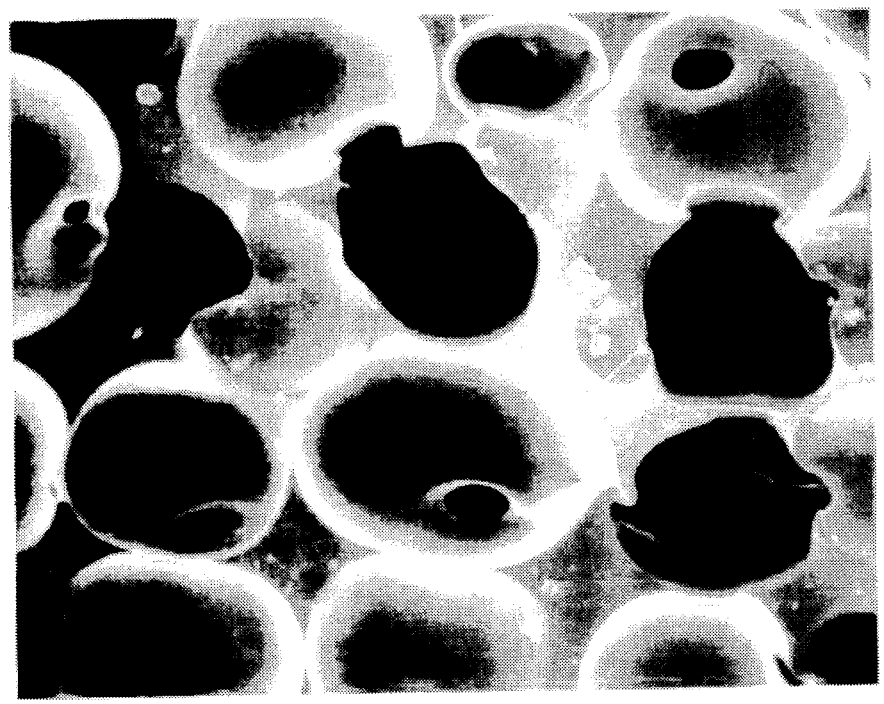
FIG. 1 is a scanning electron micrograph of a section through a polyurethane foam according to the invention.

The foam had a density of 0.38 g/cm$^3$, an elongation at break of 930%, and was capable of absorbing 10.7 g saline/g. FIG. 1 shows a scanning electron micrograph (106.5x magnification) of a section through the foam. It can be seen that the cells are of very regular size, and the pores in the cell walls are generally circular with very smooth margins. The foam is thus eminently suitable for use as a wound contact layer.

Figure 2:
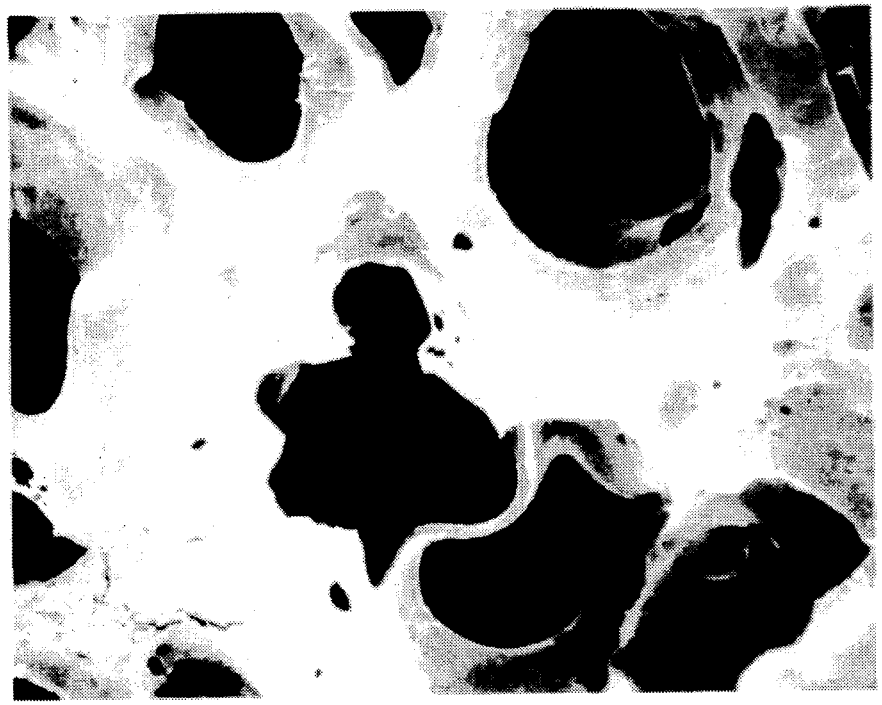
FIG. 2 is a scanning electron micrograph of a section through a prior art polyurethane foam.

By way of comparison, FIG. 2 is a scanning electron micrograph (120x magnification) of a section through a commercially available dressing, which is believed to be made in accordance with EP-A-0335669. The cells and the pores between them are seen to be highly irregular in shape.

EXAMPLE 2: COMPARATIVE

Figure 3:
FIG. 3 is a scanning electron micrograph of a section through a polyurethane foam which was prepared using an isocyanate-capped prepolymer having an NCO content greater than 1.2.

The procedure of Example 1 was followed, except that Hypol 2002 was used as the prepolymer. Hypol 2002 has an NCO content of 1.6 meq/g. The resulting product exhibited the gross porosity described in EP-A-0335669, and was quite unsuitable for use as an absorbent wound contact layer. FIG. 3, which is a scanning electron micrograph (126x magnification) of a section through the product, shows a highly reticulated structure, rather than distinct cells.

EXAMPLE 3: EFFECT OF ACRYLIC LATEX

Acrylic emulsion (PRIMAL N-582; 10 g) was mixed with deionised water (34 g) with a spatula in a disposable cup. Methanol (6 g) was added to HYPOL Hydrogel prepolymer (50 g) in a disposable cup and mixed thoroughly for a few seconds. The acrylic/water mixture was then added to the HYPOL mixture and stirred. The foaming mixture was then treated as described above in Example 1.

The resulting foam had a density of 0.35 g/cm$^3$, an elongation at break of 1000%, and was capable of absorbing 8.5 g saline/g. The addition of the acrylic latex thus reduced absorbency to only a comparatively small extent.

Figure 4:
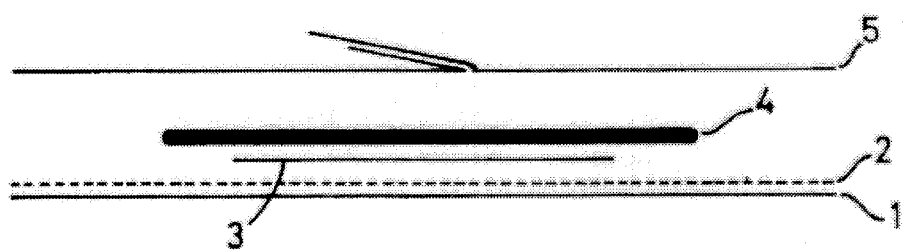
FIG. 4 is a schematic section through a dressing according to the invention.

The foam produced in this example was formed into a wound dressing as shown schematically in FIG. 4. The dressing comprises a backing layer 1, in the form of a conformable, waterproof, extensible breathable film or foam, which is coated with a continuous or discontinuous layer of skin friendly adhesive 2. Centrally located on the backing layer 1 is a wicking layer 3 of absorbent material, and this in turn is covered by a wound contacting layer 4 of the polyurethane foam. Prior to use, the adhesive layer 2 and the wound contacting layer 4 are covered by a protective release paper 5 of conventional form. This is removed when the dressing is required, to expose the adhesive-coated margins of the backing layer 1 around the wound contacting layer.

EXAMPLE 4: EFFECT OF DIFFERENT PREPOLYMER CONCENTRATIONS

Five different formulations of wound-contacting layer were prepared by the method of Example 1. Each used water and HYPOL Hydrogel prepolymer in differing proportions, together with 10% w/w of acrylic emulsion (PRIMAL N-582) and 6% w/w methanol. The wound-contacting layers so prepared were then tested for absorbency. The results were as follows:

| Percentage HYPOL hydrogel | 70% | 65% | 50% | 40% | 35% |
| --- | --- | --- | --- | --- | --- |
| Absorbency Saline g/g | 3.2 | 5.6 | 8.5 | 7.8 | 3.7 |

EXAMPLES 5–7

Further formulations based on Hypol Hydrogel prepolymer, water, methanol, and optionally PRIMAL N-582 were prepared in accordance with Example 3 as follows:

| Ex. No. | Hypol (g) | Water (g) | MeOH (g) | Acrylic (g) |
| --- | --- | --- | --- | --- |
| 5 | 25 | 20 | 5 | — |
| 6 | 25 | 21 | 4 | — |
| 7 | 25 | 17 | 3 | 5 |

In each case, the resulting foam was highly absorbent, highly conformable, and had a density of at least 0.28 g/cm$^3$. The individual data were as follows:

| Ex. No | Elongation (%) | Density (g/cm$^3$) | Absorbency (g/g) |
| --- | --- | --- | --- |
| 5 | 2350 | 0.6 | 5.5 |
| 6 | 2000 | 0.32 | 6.5 |
| 7 | 1000 | 0.35 | 8.5 |

EXAMPLES 8–15

The following examples illustrate the use of ethanol in conjunction with Levagel polyol in the method described above in Example 1.

| Ex. No. | Hypol (g) | Water (g) | EtOH (g) | Levagel (g) |
|---|---|---|---|---|
| 8 | 25 | 18.5 | .4 | 2.5 |
| 9 | 24 | 18.5 | .5 | 2.5 |
| 10 | 24 | 16 | 5 | 5 |
| 11 | 11.5 | 8 | 3 | 2.5 |
| 12 | 24 | 16 | 7.5 | 2.5 |
| 13 | 25 | 14.5 | 7 | 7 |
| 14 | 25 | 15 | 6.5 | 3.5 |

Again, each example produced a highly conformable, absorbent foam with a density of at least 0.28 g/cm$^3$.

EXAMPLES 15–23: EFFECT OF ALCOHOL ON CURE RATE

Formulations were prepared as described in Example 3, comprising 25 g HYPOL Hydrogel, 5 g Primal N-582 acrylic latex, alcohol in amounts of 3 g, 5 g or 7.5 g, and water to a total of 50 g. The time taken for the foam to cure was measured, with the following results:

| Ex. No. | Alcohol | Amount (g) | Time to cure (min) |
|---|---|---|---|
| 15 | Methanol | 3 | 2.0 |
| 16 | " | 5 | 3.5 |
| 17 | " | 7.5 | No cure |
| 18 | Ethanol | 3 | 2.0 |
| 19 | " | 5 | 2.3 |
| 20 | " | 7.5 | 3.7 |
| 21 | Propanol | 3 | 1.6 |
| 22 | " | 5 | 2.2 |
| 23 | " | 7.5 | 3.5 |

Methanol is seen to reduce the cure rate to the greatest extent, and it also has the advantage of the lowest boiling point, allowing easy removal of excess alcohol from the foam after curing.

I claim:

1. A method of forming and packaging a wound dressing comprising a polyurethane foam suitable for use as a wound-contacting layer, said method comprising mixing 1 part by weight of an isocyanate-capped prepolymer having from 0.5 to 1.2 meq NCO groups/g with from 0.4 to 1.0 parts by weight of water in the presence of from 0.05 to 0.4 parts by weight of $C_1$ to $C_3$ monohydric alcohol thereby forming the foam, then drying the foam, leaving less than 1% by weight of alcohol in the foam, and then packaging the wound dressing in a sterile, bacteria proof envelope.

2. A method according to claim 1 wherein the monohydric alcohol is methanol.

3. A method according to claim 1 wherein the isocyanate-capped prepolymer is an isocyanate-capped polyether prepolymer.

4. A method according to claim 2 wherein the isocyanate-capped prepolymer is an isocyanate-capped polyether prepolymer.

5. A method according to claim 3 wherein the isocyanate-capped polyether prepolymer is an isocyanate-capped ethyleneoxy/propyleneoxy copolymer.

6. A method according to claim 4 wherein the isocyanate-capped polyether prepolymer is an isocyanate-capped ethyleneoxy/propyleneoxy copolymer.

7. A method according to claim 1 wherein one part by weight of the isocyanate-capped prepolymer is mixed with from 0.6 to 0.9 parts by weight of water.

8. A method according to claim 1 wherein one part by weight of the isocyanate-capped prepolymer is mixed with water in the presence of from 0.05 to 0.25 parts by weight of methanol or from 0.1 to 0.3 parts by weight of ethanol.

9. A method according to claim 1 wherein one part by weight of the isocyanate-capped prepolymer is mixed with water in the presence of from 0.05 to 0.25 parts by weight of methanol or from 0.1 to 0.3 parts by weight of ethanol.

10. A method according to claim 3 wherein one part by weight of the isocyanate-capped prepolymer is mixed with water in the presence of from 0.05 to 0.25 parts by weight of methanol or from 0.1 to 0.3 parts by weight of ethanol.

11. A sterile wound dressing comprising a polyurethane foam formed by reacting an isocyanate-capped prepolymer with water in the presence of a $C_1$ to $C_3$ monohydric alcohol and then drying the foam to leave less than 1% by weight of alcohol in the foam, the foam having a density of at least 0.28 g/cm$^3$ and an elongation at break of at least 150%, the wound dressing being packaged in a sterile, bacteria proof envelope.

12. A wound dressing according to claim 11 wherein the foam has a density in the range of 0.32 to 0.48 g/cm$^3$.

13. A wound dressing according to claim 11 wherein the foam has an elongation at break in the range of 500 to 2,000%.

14. A wound dressing according to claim 11 wherein the foam has an absorbency of at least 3 g saline/g.

15. A wound dressing according to claim 11 wherein the foam has a swellability upon absorption of water of at least 200%.

16. A wound dressing according to claim 15 wherein the foam has a swellability of at least 400%.

17. A wound dressing according to claim 15 wherein the foam has a swellability between 400% to 800%.

18. A wound dressing according to claim 11 wherein the foam has a density of at least 0.35 gm/cm$^3$.

19. A wound dressing according to claim 11 wherein the foam has a density of about 0.35 gm/cm$^3$.

20. A wound dressing according to claim 11 wherein the foam has an elongation at break of at least 300%.

21. A wound dressing according to claim 11 wherein the polyurethane foam is formed by reacting 1 part by weight of an isocyanate-capped prepolymer having from 0.5 to 1.2 meq NCO groups/g with from 0.4 to 1.0 parts by weight of water in the presence of from 0.05 to 0.4 parts by weight of a $C_1$ to $C_3$ monohydric alcohol, and then drying the foam to leave less than 1% by weight of alcohol in the foam.

22. A sterile wound dressing comprising a polyurethane foam formed by reacting an isocyanate-capped prepolymer with water in the presence of a $C_1$ to $C_3$ monohydric alcohol and then drying the foam to leave less than 1% by weight of alcohol in the foam, the foam having a density in the range of 0.32 to 0.48 g/cm$^3$, an elongation at break in the range of 500 to 2,000%, an absorbency of at least 3 g saline/g, and a swellability upon absorption of water of at least 200%, the wound dressing being packaged in a sterile, bacteria proof envelope.

23. A method of forming and packaging a wound dressing comprising a polyurethane foam suitable for use as a wound-contacting layer, said method consisting of, mixing 1 part by weight of an isocyanate-capped prepolymer having from 0.5 to 1.2 meq NCO groups/g with from 0.4 to 1.0 parts by weight of water in the presence of from 0.05 to 0.4 parts by weight of $C_1$ to $C_3$ monohydric alcohol thereby forming the foam, then drying the foam, leaving less than 1% by weight of alcohol in the foam, and then packaging the wound dressing in a sterile, bacteria proof envelope.

\* \* \* \* \*